United States Patent [19]

Halko et al.

[11] 4,105,334
[45] Aug. 8, 1978

[54] OPTICAL DETECTOR

[75] Inventors: Richard A. Halko, Flanders; John J. Heigl, Short Hills, both of N.J.

[73] Assignee: Exxon Research & Engineering Co., Linden, N.J.

[21] Appl. No.: 712,536

[22] Filed: Aug. 9, 1976

[51] Int. Cl.² ........................................... G01N 21/00
[52] U.S. Cl. .................................. 356/104; 250/574; 356/70
[58] Field of Search ................. 356/70, 103, 104, 208; 250/564, 573, 574, 576

[56] References Cited

U.S. PATENT DOCUMENTS

| | | |
|---|---|---|
| 2,692,528 | 10/1954 | Uhl ........................................ 356/104 |
| 3,200,700 | 8/1965 | Topol ..................................... 356/104 |
| 3,526,461 | 9/1970 | Lindahl et al. ..................... 356/103 X |
| 3,691,391 | 9/1972 | Kishi ................................. 356/208 X |
| 3,899,688 | 8/1975 | Périères ........................... 250/574 X |

FOREIGN PATENT DOCUMENTS 440,748  1/1968  Switzerland ............................. 356/103

*Primary Examiner*—John K. Corbin
*Assistant Examiner*—Matthew W. Koren
*Attorney, Agent, or Firm*—F. Donald Paris

[57] ABSTRACT

An analyzer and method for measuring the properties of a liquid sample, such as the monitoring of water streams for oil detection as in ballast water monitoring onboard tankers, wherein a sample stream is passed through a nonreflective chamber where it is illuminated by suitable light such as fiber optic. The stream is detected either visually through a viewing port or photoelectrically for desired properties or characteristics as the flowing sample stream fails by gravity through the chamber to collection pit.

17 Claims, 2 Drawing Figures

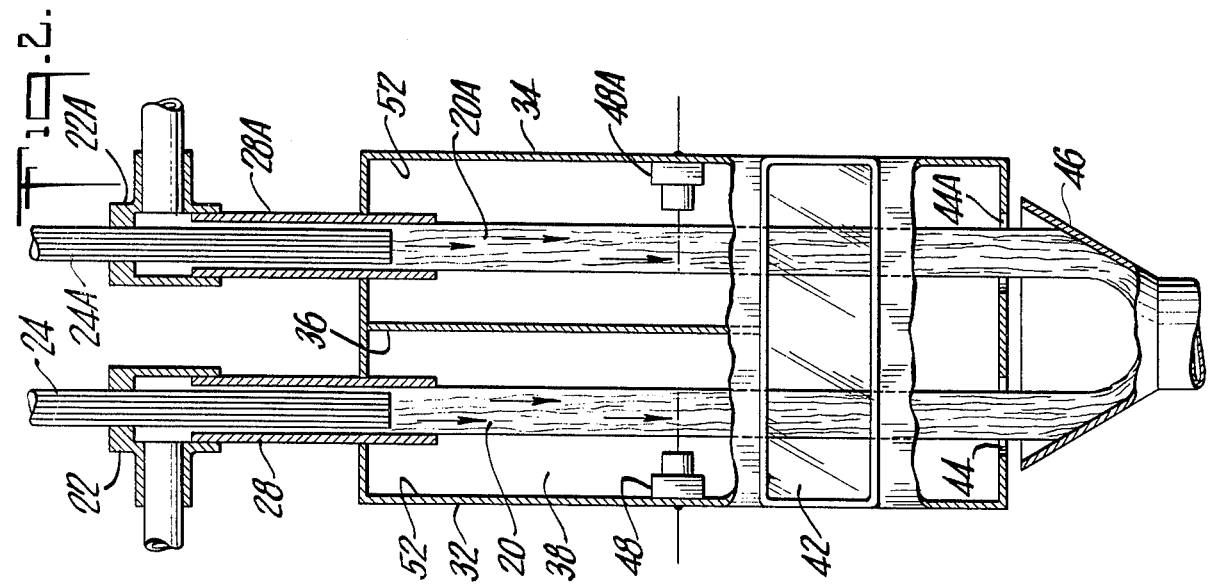
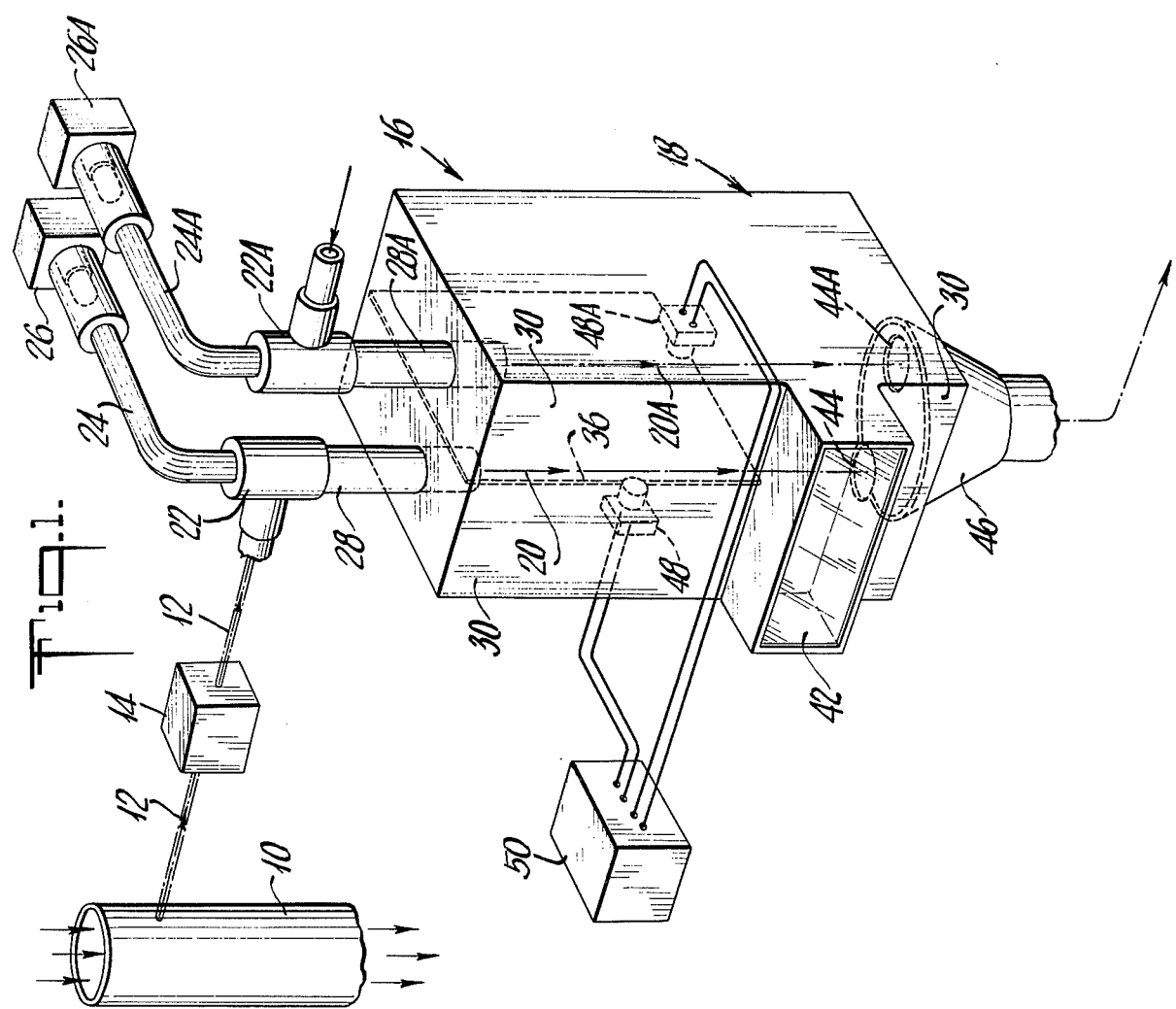

OPTICAL DETECTOR

BACKGROUND OF THE INVENTION

It is common practice in the field of measuring properties or characteristics of liquid streams to extract a sample of the stream and then proceeding to analyze it in a laboratory. Other approaches used such as in monitoring of water streams for oil detection, e.g. ballast water monitoring onboard tankers, rely on a variety of different techniques and systems such as disclosed in U.S. Pat. Nos. 3,710,111; 3,612,887; and 3,581,085.

Other prior art typical of this area include systems such as disclosed in U.S. Pat. No. 2,892,378, which employs an indicating turbidimeter for detecting and measuring the turbidity of a fluid or U.S. Pat. No. 3,306,157 which also discloses a turbidimeter for sensing turbidity of a continuously-flowing fluid sample, wherein light rays project through a lens into the liquid under test and the intensities of the projected beam are reflected to photocells which provide an indication of the turbidity. Still yet a further prior art patent is that of U.S. Pat. No. 3,617,757 wherein light rays are projected through a liquid undergoing test which is received by a photocell for providing an indication of characteristic of liquid. Further prior art located in respect of the invention include the following U.S. patents:

U.S. Pat. No. 3,246,145—Higgins
U.S. Pat. No. 3,659,943—Goolsby
U.S. Pat. No. 3,714,444—Carr et al.
U.S. Pat. No. 3,734,629—Griffiths et al.
U.S. Pat. No. 3,885,418—Kriebel

SUMMARY OF THE INVENTION

The present invention relates to the detection of properties of a liquid sample and more particularly to an electro-visual system for detecting such properties. Specifically, the invention relates to a stream of sample liquid flowing through an appropriate device termed herein an electro-visual turbidimeter, which will detect or measure the optical properties of the liquid sample when illuminated. The illumination can be accomplished by inserting a probe such as a fiber optic probe upstream from the point of observation or of the stream detection point and then detecting either visually or photoelectrically at the point where the stream is freely falling from the sample tube prior to its entry into the collection sump situated below. This is accomplished with a minimum of interference in background light and maximum illumination of the sample stream which permits the detection to be done in an efficient and accurate manner. Basically, the sample stream is extracted and flowed through a tube and then permitted to fall freely through a chamber and during its free fall path the properties are measured. If desired, the measurements can be recorded or otherwise displayed by an appropriate device, e.g. graphic recorder or indicating meter, which will show the measured or detected properties and enable one to readily determine whether they meet the desired requirements. It is also contemplated that the sample stream properties can be compared with those of a standard or reference stream. The invention provides a visual and electronic detection technique which is free from any fouling that would obscure visual observation of the properties of the freely falling sample stream and also is intrinsically safe from an operational viewpoint.

Accordingly, there is provided an improved detector of the electro-visual type for detecting physical properties of a liquid such as the oil content in a water stream, (e.g., ballast on a tanker) which is more efficient than the prior art devices heretofore known. Other advantages and the nature, construction and arrangement and operation of the present invention will be apparent from the following detailed description of the disclosed embodiments when read in conjunction with the accompanying drawings.

BRIEF DESCRIPTION OF THE DRAWINGS

FIG. 1 is a perspective view of a detector of the electro-visual type constructed and arranged in accordance with the present invention.

FIG. 2 is a cross-sectional view of the detector of FIG. 1, particularly illustrating the measuring/viewing chamber.

DESCRIPTION OF THE PREFERRED EMBODIMENT

Referring now to the drawings wherein like parts are designated by the same reference numeral throughout the several views, there is shown in FIG. 1 a detector device and system according to the present invention used in connection with a flowing stream which typically might comprise monitoring a water stream for oil detection, for example, ballast water monitoring on board a tanker. The stream being monitored is shown flowing through a process or conduit line 10 and is withdrawn by conventional sample extraction probe (not shown). The sample is passed through a sample line 12 which includes a sample conditioning unit 14. The unit may comprise a mixer or the like which would function to insure that the sample is uniformly mixed. The other end of the sample line is connected for directing the sample stream through the detector generally designated 16 of the present invention. The detector includes a measuring and viewing chamber 18 through which the stream freely flows as shown at 20 (see FIG. 2). The sample stream enters the detector through a T-shaped inlet coupling 22 essentially at right angle relative to the stream path through the chamber. The stream is turned ninety degrees from its entry direction in the downward direction and falls freely (by gravity) through the chamber. This eliminates any contact of the stream with optical surfaces which could be subject to fouling and might interfere with the visual appearance of the sample stream as it falls. The top of the T inlet is connected with a fiber optic light pipe 24, which extends through the inlet axially being disposed substantially in the center of the sample stream as it is turned downward, as best shown in FIG. 2. The fiber optic typically may comprise a single or bundle of fibers which are well known in the art and are commercially available. A suitable light source 26 such as a conventional incandescent type bulb is connected at the free end of the fiber optic for transmitting light through the light pipe 24 upon energization and causing the freely falling stream to become illuminated internally. The light sources themselves are contained within housings which are intrinsically safe or in an area which is remote from the hazardous location. Preferably, the light pipe extends through the inlet and partially into the chamber 18 so that it provides sufficient illumination of the stream. After the sample stream passes transversely into the inlet 22, its flow is directed downwardly through the open bottom of the inlet which also contains the free end of the light pipe 24. The inlet coupling 22 and fiber optic light pipe 24 are supported by a support member 28, which is mounted to the chamber 18 in the top surface thereof in a conventional fashion (e.g. welded in an opening). The chamber essentially comprises a front panel 30, side members 32 and 34, and includes a solid central partition 36 extending between the front and rear walls for dividing the chamber into transverse compartments 38 and 40. At a location in the front panel or wall of the chamber 16 there is provided a viewing port 42, shown as rectangular although other configurations also are acceptable, which comprises a clear glass or plastic member to enable visual observation of at least the freely falling stream 20. The viewing port 42 is situated at the bottom end of the chamber spaced from the end of the light pipe so that an operator can conveniently observe the condition of the sampled stream. The bottom of the chamber has an opening vertically aligned with the bottom exit end of the inlet coupling 22 and through which the stream passes. A collection pit or sump 46 is disposed directly below this opening for receiving and collecting the freely falling sample stream, whereupon it can be disposed of in an appropriate manner such as by passing it on to a further larger collection or storage chamber or the like. A second T-shaped inlet coupling 22A is provided for communication with the other compartment 40. A fiber optic light pipe 24A connected at one end to a light source 26A has its other end extending axially through the coupling 22A and terminating within the support 28A which is supported on the other side of the chamber 16 similar to the arrangement for the light pipe 24. A clear stream sample (which may be obtained from any appropriate source) i.e. one which has been determined to meet established standards or have desired properties, is passed transversely into the inlet coupling 22A and is permitted to fall freely downward (similar to the sample stream 20 as best shown in FIG. 2) as illustrated by the stream 20A (see FIG. 2) through the chamber reference compartment 40, thereby permitting a visual observation and comparison to be made of the clear stream 20A in comparison with the sample stream 20. The clear sample stream also passes into the sump 46 through the opening 44 at the bottom of compartment 40. At locations directly above the viewing point are provided a pair of opposed light sensitive detectors 48 and 48A which are mounted in the side walls 32 and 34 of the chamber compartments 38 and 40 respectively for sensing the light intensity of the freely flowing sample and clear streams 20, 20A. These detectors typically may comprise photoresistive, photoelectric or other such conventional elements connected electrically to a conventional measuring instrument 50 which typically may include a bridge circuit and/or amplifier. The instrument's function is to condition the signal prior to delivery to the read-out device. The light transmitted from the light sources 26, 26A will illuminate the freely falling sample stream 20 and the clear stream 20A internally because of the disposition of the light pipes within the falling streams. The light will be scattered as a result of any component contained within the sample stream which will thereby make the streams appear more or less bright to an observer looking through the viewing port 42. The increase in scattered light intensity is sensed electronically by the light sensitive detectors 48, 48A. While not necessary to the invention, in a preferred embodiment the additional reference standard for comparison in the form of a freely falling clear stream 20A provides a convenient way of assessing the properties of the sample stream 20. In order to minimize any reflection by the illuminating light which may cause false readings, the internal surfaces of the interior of the chamber compartments 38, 40 can be lined as shown at 52 with a suitable dark nonreflective material.

Thus, a visual comparison can be made between the sample stream and the clear stream via the viewing port 42 merely by comparing the streams or by comparison of the sample stream to an appropriate chart. If it is determined that the sample stream contains an excessive amount of an undesirable property (e.g., oil) appropriate measures can be taken to correct this. Such measures do not form part of the present invention. The alternate arrangement disclosed heretofore comprises the use of the light sensitive detectors connected to a conventional measuring instrument which would photoelectronically detect the amount of undesirable property in the stream and convey a representative electrical signal for comparison with a reference signal indicative of the clear stream. The instrument then would provide a readout which would indicate whether additional or any action was required to correct the situation, such as if the readout exceeded a predetermined level.

While a preferred embodiment of the present invention has been shown and certain variations mentioned, further modifications and variations in the construction and/or arrangement of the invention may present themselves to those skilled in the art upon the reading of this disclosure. It is therefore intended that such variations and/or modifications fall within the scope of the present invention which is better defined by reference to the appended claims.

What is claimed is:

1. Apparatus for use in detecting a selected physical property of a flowing liquid stream comprising: a chamber having first inlet means for receiving a sample of said stream and passing said sample as a freely falling stream through said chamber; optic means for internally illuminating the freely falling sample in a substantially axial direction of flow as it passes through said chamber, whereby the light from said optic means will scatter as a function of said property; and means disposed relative to the scattered light for enabling detection of said property of said freely falling stream.

2. The detector of claim 1 including second inlet means to said chamber for receiving a reference stream and passing said stream as a freely falling stream in parallel with said sample stream through said chamber; and said optic means internally illuminating said reference stream in a substantially axial direction relative to the passage of said reference stream through said chamber.

3. The detector of claim 2 wherein said chamber includes a partition forming separate compartments for said sample stream and said reference stream.

4. The detector of claim 3 wherein said chamber including said partition is lined with nonreflective material for minimizing reflection of scattered light within said chamber.

5. The detector of claim 3 including first light sensitive detector means for sensing the scattered light intensity of said freely falling stream and second light sensitive detector means for sensing the scattered light intensity of said reference stream.

6. The detector of claim 5 including comparison means connected with said first and second light sensitive detector means for comparing the sensed scattered light intensity of said sample stream and said reference stream.

7. The detector of claim 1 wherein said first inlet means comprises a T-shaped member having a main axis including an inlet for receiving said sample stream transversely of said outlet and directing said stream to flow axially from said outlet through said chamber, said optic means extending axially into said T-shaped member past said inlet toward said outlet and disposed internally of said free falling sample stream as it exits said outlet.

8. The detector of claim 7 wherein said optic means comprises a fiber optic.

9. The detector of claim 1 wherein said chamber includes nonreflective material disposed on the walls of said chamber for minimizing reflection of said scattered light within said chamber.

10. The detector of claim 1 wherein said optic means is substantially axially aligned with the direction of flow of said freely falling stream through said chamber.

11. The detector of claim 1 wherein said optic means is located upstream of said freely falling stream through said chamber.

12. The detector of claim 1 wherein said optic means is substantially axially aligned with the center of the freely falling sample stream.

13. A detector for determining selected physical properties of a flowing liquid stream comprising a chamber having front, side, rear, top and bottom walls, partition means extending between said front and rear walls for separating said chamber into first and second transversely disposed compartments, first inlet means for said first compartment in said top wall and second inlet means for said second compartment in said top wall transverse of said first inlet means, said first and second outlet means including an outlet end having an axis and an inlet end disposed substantially perpendicular to the axis of said outlet end, outlet means in said bottom wall for said first and second compartments, optic means mounted with said first and second inlet means for generating illumination light in the direction of the axes of said outlet ends of said first and second inlet means for internally axially illuminating liquid streams passing from said outlet ends, a viewing port in said front wall of said chamber and first and second light sensitive detecting means mounted downstream from said outlet ends in said side walls for said first and second compartments, respectively.

14. A method for measuring the optical properties of a liquid sample comprising the steps of
 (a) withdrawing a predetermined sample from a flowing stream;
 (b) passing said sample into a chamber and permitting said sample to fall freely in an axial direction through said chamber;
 (c) internally illuminating said free falling sample stream in said axial direction as it passes through said chamber; and
 (d) determining the scattered light intensity of said free falling stream.

15. The method of claim 14 including the step of passing a free falling reference stream through said chamber and internally axially illuminating said reference stream for enabling comparison of the scattered light intensity of said free falling sample and reference streams.

16. A detector for determining a selected physical property of a flowing liquid stream comprising: a chamber having first inlet means for receiving a sample of said stream and passing said sample as a freely falling stream through said chamber; optic means for internally illuminating said freely falling sample in a substantially axial direction of flow as it passes through said chamber; and means for detecting said property of said freely falling stream comprising light sensitive detector means for sensing the amount of scattered light intensity.

17. A detector for determining a selected physical property of a flowing liquid stream comprising: a chamber having first inlet means for receiving a sample of said stream and passing said sample as a freely falling stream through said chamber; optic means for internally illuminating the freely falling sample in a substantially axial direction of flow as it passes through said chamber; and said chamber including viewing port means for enabling visual observation of said sample stream.

* * * * *